United States Patent
Lu et al.

(10) Patent No.: US 10,041,866 B2
(45) Date of Patent: Aug. 7, 2018

(54) REPRODUCIBLE SAMPLE PREPARATION METHOD FOR QUANTITATIVE STAIN DETECTION

(71) Applicant: UNIVERSITY OF SOUTH CAROLINA, Columbia, SC (US)

(72) Inventors: Zhenyu Lu, Columbia, SC (US); Brianna Cassidy, Columbia, SC (US); Katherine Witherspoon, Columbia, SC (US); Stephanie Dejong, Ripon, CA (US); Raymond G. Belliveau, III, Columbia, SC (US); Michael Myrick, Columbia, SC (US); Stephen L. Morgan, Columbia, SC (US)

(73) Assignee: University of South Carolina

( * ) Notice: Subject to any disclaimer, the term of this patent is extended or adjusted under 35 U.S.C. 154(b) by 243 days.

(21) Appl. No.: 15/136,252

(22) Filed: Apr. 22, 2016

(65) Prior Publication Data

US 2016/0312401 A1    Oct. 27, 2016

Related U.S. Application Data

(60) Provisional application No. 62/152,075, filed on Apr. 24, 2015.

(51) Int. Cl.
  *G01N 1/30* (2006.01)
  *G01N 33/49* (2006.01)
  *B33Y 10/00* (2015.01)

(52) U.S. Cl.
  CPC .............. *G01N 1/30* (2013.01); *G01N 33/49* (2013.01); *B33Y 10/00* (2014.12)

(58) Field of Classification Search
  CPC .................................. G01N 1/30; G01N 33/49
  See application file for complete search history.

(56) References Cited

U.S. PATENT DOCUMENTS

| | | | |
|---|---|---|---|
| 3,562,524 A | 2/1971 | Moore et al. | |
| 3,684,867 A | 8/1972 | Acker | |
| 3,783,284 A | 1/1974 | McCormack | |
| 4,201,914 A | 5/1980 | Perren | |
| 4,333,008 A | 6/1982 | Misek | |
| 5,179,422 A | 1/1993 | Peterson | |
| 5,247,185 A | 9/1993 | Herrera et al. | |
| 5,312,521 A | 5/1994 | Fraas et al. | |
| 5,504,332 A | 4/1996 | Richmond et al. | |
| 5,900,634 A | 5/1999 | Soloman | |
| 5,945,676 A | 8/1999 | Khalil et al. | |
| 5,946,088 A | 8/1999 | Aldridge | |
| 6,260,997 B1 | 7/2001 | Claybourn et al. | |
| 6,370,327 B1 | 4/2002 | Seguy et al. | |

(Continued)

OTHER PUBLICATIONS

Andrasko, J., "The estimation of the age of bloodstains by HPLC analysis," *J. Forensic. Sci.*, (1997) 42 (4) pp. 601-607.

(Continued)

*Primary Examiner* — Cachet I Sellman
(74) *Attorney, Agent, or Firm* — Dority & Manning, P.A.

(57) ABSTRACT

A stain-barrier is described along with methods of its application to a fabric. The stain barrier reduces variability between samples of different dilution or fabric type so that limits of stain detection can be assigned more accurately and precisely and stain detection techniques can be transparently compared.

18 Claims, 2 Drawing Sheets

(56) References Cited

U.S. PATENT DOCUMENTS

| | | | |
|---|---|---|---|
| 6,490,035 | B1 | 12/2002 | Folestad et al. |
| 6,504,943 | B1 | 1/2003 | Sweatt et al. |
| 6,517,230 | B1 | 2/2003 | Afnan et al. |
| 6,776,517 | B2 | 8/2004 | Afnan et al. |
| 6,849,460 | B2 | 2/2005 | McFarland et al. |
| 7,123,360 | B2 | 10/2006 | Treado et al. |
| 7,417,228 | B2 | 8/2008 | Belov |
| 7,489,252 | B2 | 2/2009 | Long et al. |
| 7,595,734 | B2 | 9/2009 | Long et al. |
| 7,623,235 | B2 | 11/2009 | Ho et al. |
| 7,623,237 | B1 | 11/2009 | Liphardt et al. |
| 7,671,975 | B2 | 3/2010 | Mangan et al. |
| 2003/0124936 | A1* | 7/2003 | Potts .......... A61F 13/15634 442/327 |
| 2004/0239923 | A1 | 12/2004 | Adams et al. |
| 2005/0032235 | A1 | 2/2005 | Tummala et al. |
| 2005/0062006 | A1 | 3/2005 | Wilfert |
| 2006/0060278 | A1 | 3/2006 | Treado et al. |
| 2006/0106317 | A1 | 5/2006 | McConnell et al. |
| 2007/0021670 | A1 | 1/2007 | Mandelis et al. |
| 2007/0152154 | A1 | 7/2007 | DeCamp et al. |
| 2007/0201136 | A1 | 8/2007 | Myrick et al. |
| 2008/0094616 | A1 | 4/2008 | Tanaka |
| 2008/0225303 | A1 | 9/2008 | Lampalzer |
| 2008/0276687 | A1 | 11/2008 | Myrick et al. |
| 2009/0073433 | A1 | 3/2009 | Myrick et al. |
| 2009/0140144 | A1 | 6/2009 | Myrick et al. |
| 2009/0216504 | A1 | 8/2009 | Myrick et al. |
| 2009/0219512 | A1 | 9/2009 | Myrick et al. |
| 2009/0219538 | A1 | 9/2009 | Myrick et al. |
| 2009/0219539 | A1 | 9/2009 | Myrick et al. |
| 2009/0219597 | A1 | 9/2009 | Myrick et al. |
| 2009/0240222 | A1* | 9/2009 | Tomoko .......... A61F 13/51104 604/365 |
| 2009/0245321 | A1 | 10/2009 | Ringermacher |
| 2009/0250613 | A1 | 10/2009 | Myrick et al. |
| 2009/0303471 | A1 | 12/2009 | Treado et al. |
| 2009/0318815 | A1 | 12/2009 | Barnes et al. |
| 2010/0042348 | A1 | 2/2010 | Bakker |
| 2010/0195105 | A1 | 8/2010 | Myrick et al. |
| 2010/0265320 | A1 | 10/2010 | Treado et al. |
| 2011/0007774 | A1 | 1/2011 | Hatcher |
| 2011/0090342 | A1 | 4/2011 | Myrick et al. |
| 2011/0284735 | A1* | 11/2011 | Van Berkel .......... G01N 1/4055 250/282 |
| 2012/0138820 | A1* | 6/2012 | Plese .......... G01N 21/64 250/459.1 |
| 2013/0230821 | A1 | 9/2013 | Brown |

OTHER PUBLICATIONS

Blum, etal.; "A new high-performance reagent and procedure for latent bloodstain detection based on luminol chemiluminescence," *Canadian Society of Forensic Science* (2006) 39(3) pp. 81-100.
Botonjic-Sehic, etal; "Forensic application of near infrared spectroscopy: aging of bloodstains," *Spectroscopy* (2009) 24 pp. 42-48.
Bremmer, etal; "Forensic quest for age determination of bloodstains," *Forensic Sci. Int.*, (2012) 216 pp. 1-11.
Bruno A. Olshausen, "Aliasing"—handout prepared and distributed for PSC 129 at the University of California, Berkeley, dated 2000, retrieved online from http://redwood.berkeley.edu/bruno/npb261/aliasing.pdf Jun. 5, 2015.
Budowle, etal.; "The presumptive reagent fluorescein for detection of dilute bloodstains and subsequent STR typing of recovered DNA," *J Forensic Sci* (2000) 45(5) pp. 1090-1092.
Edelman, etal.; "Identification and age estimation of blood stains on colored backgrounds by near infrared spectroscopy," *Forensic Sci. Int.*, (2012) 220 pp. 239-244.
Egan, etal.; "Measurement of carboxyhemoglobin in forensic blood samples using UV/VIS spectrometry and improved principal component regression," *Applied Spectroscopy* (1999) 53(2) pp. 218-225.
Finnis, J.; Lewis, J.; Davidson, A. Comparison of methods for visualizing blood on dark surfaces. Science and Justice 2013:53:178-186.
Garofano, etal; "A comparative study of the sensitivity and specificity of luminol and fluorescein on diluted and aged bloodstains and subsequent STRs typing," *International Congress Series* (2006) 1288 pp. 657-659.
Gnyaneshwari; "An evaluation of luminol formulations and their effect on DNA profiling," *Int J Legal Med* (2013) 127 pp. 723-729.
Hanson et al.; "A blue spectral shift of the hemoglobin soret band correlates with the age of dried bloodstains," *Plos ONE* (2010) 5 [e12830].
Lu, etal.; "Using Fourier transform infrared spectroscopy to estimate blood age under different environmental conditions," Abstract No. 2170-6; Univ. of South Carolina; Mar. 11, 2015 (abst. only).
Inoue, etal.; "A new marker for estimation of bloodstain age by high performance liquid chromatography," *Forensic Sci. Int.*, (1992) 57 pp. 17-27.
Inoue, etal; "Identification of fetal hemoglobin and simultaneous estimation of bloodstain age by high-performance liquid chromatography," *Int. J. Legal Med.*, (1991) 104 pp. 127-131.
Kind, etal.; "Estimation of the age of dried blood stains by a spectrophotometric method," *Forensic Sci.* (1972) 1 pp. 27-54.
Matsuoka, etal.; "Estimation of bloodstain age by rapid determinations of oxyhemoglobin by use of oxygen-electrode and total hemoglobin," *Biol. Pharm. Bull.* (1995) 18 pp. 1031-1035.
Mauerer, A., "Secondary Structural Change of Spray Dried Proteins with Fourier Transform Infrared Spectroscopy," Ph. D. Dissertation, Friedrich Alexander University Erlangen-Nuremberg, Erlangen, Germany.
McCutcheon, J. N., "Estimation of the age of bloodstains on polymer substrates by infrared spectroscopy," University of South Carolina, 2010.
Middlestead, etal.; "Sensitivity of the luminol test with blue denim," *J Forensic Sci* (2010) 55(5) pp. 1340-1342.
PCT International Search Report for PCT/US11/35156 dated Sep. 2, 2011, 2 pages.
PCT International Search Report for PCT/US2011/035149 dated Aug. 22, 2011, 2 pages.
Schwarz, F., "Quantitative analysis of catalase und peroxidase in bloodstain," *Int. J. Legal Med.*, (1937) 27 pp. 1-34.
Seashols, etal.; "A comparison of chemical enhancements for the detection of latent blood," *J. Forensic Sci* (2013) 58(1), pp. 130-133.
Smith, B., "Infrared spectral interpretation," *CRC press*, Washington D.C., 1999.
Su, etal.; "Mechanics of forced unfolding of proteins," *Acta Biomater* (2009).
Tobe, etal.; "Evaluation of six presumptive tests for blood, their specificity, sensitivity, and effect on high molecular-weight DNA," *J Forensic Sci* (2007) 52(1) pp. 102-109.
Webb,etal.; "A comparison of the presumptive luminol test for blood with four non-chemiluminescent forensic techniques," *Luminescence* (2006) 21(4) pp. 214-220.
Webb; "Luminol vs Bluestar: A Comparison Study of Latent Blood reagents," [Internet]. Available from: http://www.bluestar-forensic.com/pdf/en/St_Louis_comparison_study.pdf 6 pages.

* cited by examiner

REPRODUCIBLE SAMPLE PREPARATION METHOD FOR QUANTITATIVE STAIN DETECTION

CROSS REFERENCE TO RELATED APPLICATION

This Application claims filing benefit of U.S. Provisional Patent Application Ser. No. 62/152,075 having a filing date of Apr. 24, 2015, which is incorporated herein by reference for all purposes

GOVERNMENT SUPPORT CLAUSE

This invention was made with government support under 2011-IJ-CX-K055 awarded by National Institute of Justice. The government has certain rights in the invention.

BACKGROUND

Blood stains, which are among the traces encountered most frequently at crime scenes, are important for potential extraction and amplification of DNA for suspect identification, as well for spatter pattern analysis to reveal a sequence of events. Estimating the age of blood stains with good accuracy and precision has been an elusive goal for forensic investigations. Estimates of blood stain age can contribute to verify witness' statements, limit the number of suspects and confirm alibis.

Blood is composed of plasma (~53%), platelets (<1%), white blood cells (~1%), and red blood cells (~45%). Hemoglobin, an oxygen carrying protein, makes up about 90% of dried blood content. In healthy blood, hemoglobin exists in two forms: deoxyhemoglobin (Hb), which is without oxygen, and oxyhemoglobin ($HbO_2$), which is saturated with oxygen. When blood is exposed to air, Hb is completely saturated with oxygen and converts to $HbO_2$. $HbO_2$ will irreversibly oxidize to methemoglobin (met-Hb). After that, met-Hb will denature to hemichrome (HC). During these process, changes in the secondary structure of the protein will take place. Hemoglobin is about 80% α-helix type proteins, while the other 20% are unordered coils. After aging, hemoglobin contains 60% α-helix type proteins, 30% β-sheet type proteins and 10% other types.

Many stain detection techniques exist (luminol, Bluestar®, fluorescein, hemascein, etc.). However, their limits of detection are not agreed upon and they are unable to be quantitatively compared to one another due to the inability to reproducibly create stain samples. Fourier Transform Infrared (FT-IR) spectrometry was developed to overcome the limitations encounter with the slow scanning of dispersive instruments. FT-IR employed an interferometer to produce a interferogram, which allows all of the infrared frequencies been detected simultaneously. The signal can be measured on the order of one second or so. The measured signal is digitized and then transformed from the time domain to the frequency domain. The infrared spectrum is then presented as a plot of absorbance vs. frequency.

However, one main issue still exists. The stain samples are currently made without regard to the effects of different stain dilutions and substrate properties. Thus, stain detection limits are imprecisely assigned to stain detection techniques, making it difficult to compare stain detection techniques to one another.

Further, many recent studies have attempted to assign limits of detection and/or compare the ability of different stain detection techniques. For studies like these to be successful, a method needs to exist which allows reproducible creation of stain samples. Currently, dilutions of stains are made and applied in constant aliquots, but no consideration is given to the effect diluting a liquid has on its behavior when applied to fabric. Generally, the more dilute a liquid, the further the liquid spreads when applied to a substrate. Additionally, consideration has not been given to the affect different substrates have on the spread of applied liquids. For example, a liquid of the same dilution and volume will spread to a smaller area on densely packed cotton than on a loosely woven silk. Both aforementioned phenomena affect the true dilution of the stain. The absence of a technique which controls the liquid-fabric interaction and allows production of reproducible stains has made experiments of this nature hugely imprecise. Consequently, vast ranges of detection limits have been assigned to various stain detection techniques. For example, luminol has been reported to have a bloodstain detection limit of five-millions times dilute (5) to one-hundred times dilute (4).

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which.

Figure 1:
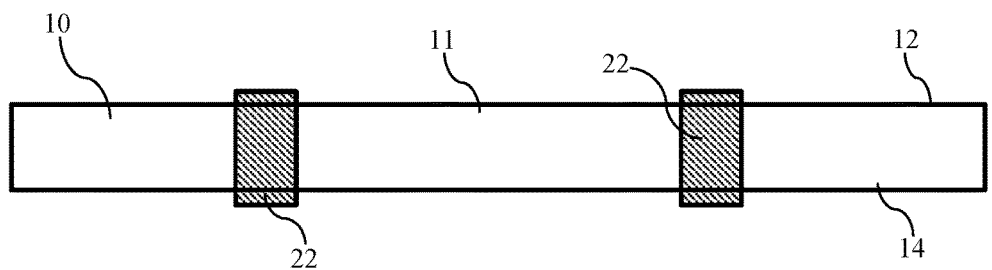
FIG. 1 is a cross-sectional view of an exemplary fabric after printing an inert polymeric composition to form the inert polymeric coating.

Repeat use of reference characters in the present specification and drawings is intended to represent the same or analogous features or elements of the present invention.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

A stain-barrier is generally provided, along with methods of its application to a fabric. The stain barrier is easily applied to fabric samples via 3-D printing methods, and limits the amount of fabric with which deposited liquid is able to interact. This stain barrier greatly reduces unwanted variability between samples of different dilution or fabric type so that limits of stain detection can be assigned more accurately and precisely and stain detection techniques can be transparently compared. Thus, the effect of stain-dilution and substrate is minimized by application of the stain-barrier to the fabric. The stain barrier allows more replicable stain samples to be made, so that stain detection techniques can be accurately compared for the first time.

The presently disclosed methods allow liquid stains to be created on fabric in a reproducible, constant manner so as to limit and hold constant the amount of fabric with which the liquid may interact. In one embodiment, an inert barrier layer is printed onto the fabric to prevent the liquid from interacting with fabric outside the intended area (i.e., the sample area). The stain barrier created using this method insures that each stain spreads within a replicable area of the fabric, thus reducing variability between samples where different dilutions of stain and different fabric substrates are implemented. Now that variation due to sample preparation can be reduced, variation due to dilution, substrate and detection response can be more clearly observed. Thus, more accurate limits of detection can to be determined for stain detection techniques and for the first time, fair comparison of stain detection techniques to one another.

Referring to FIG. 1, a fabric 10 is shown defining a first surface 12 and an opposite second surface 14. The fabric can be a woven or nonwoven fabric containing fibers. Any suitable material can be utilized to form the fabric, such as cotton fibers, nylon fibers, polyester fibers, silk fibers, etc.

Figure 3:
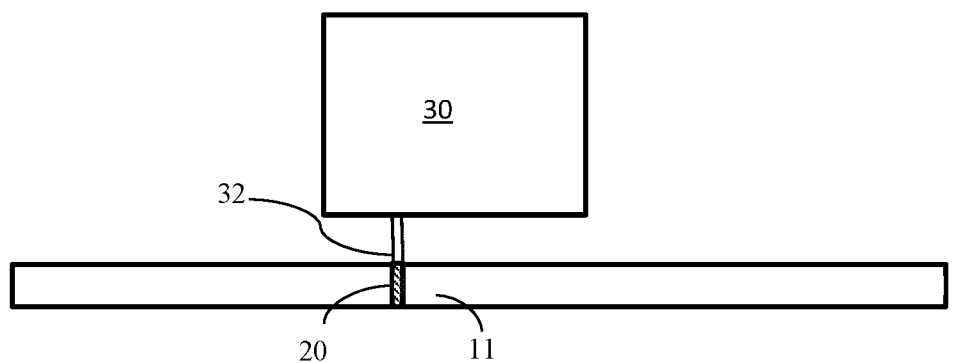
FIG. 3 illustrates an exemplary method of formation of a stain barrier utilizing a 3D printer.

FIG. 3 shows a 3D printer 30 applying a filament 32 of an inert polymeric composition 20 onto the first surface 12 of the fabric 10. The 3D printer can be any suitable 3D printer capable of printing a polymeric composition as a filament, and are readily available commercially (e.g., MakerBot® Replicator 2 from MakerBot Industries, LLC in Brooklyn, N.Y.).

The inert polymeric composition 20 generally includes a polymer having a relatively low melting point (e.g., less than 200° C., and particularly less than 150° C.). In particular, the polymer can have a melting point that is between about 100° C. and about 150° C.

Generally, printing of the inert polymeric composition 20 is performed at an extrusion temperature above the glass transition temperature ($T_g$) of the polymer such that the inert polymeric composition 20 flows into the thickness of the fabric 10 instead of remaining on the surface 12. For example, in embodiments where the polymer has a glass transition temperature that is between about 50° C. and about 100° C., the inert polymeric composition 20 can be printed at an extrusion temperature of 140° C. to about 150° C. (e.g., about 150° C.). In such an embodiment, the inert polymeric composition 20 can be printed at an extrusion temperature below the melting point of the polymer such that the filament 32 retains some cohesion to inhibit spreading laterally within the fabric 10 or on the surface 12. However, due to the extrusion temperature being above the glass transition temperature, the inert polymeric composition 20 can penetrate into the thickness of the fabric 10 instead of remaining on the surface 12, particularly when the fabric is heated before, during, and/or after printing. For example, in embodiments where the polymer has a glass transition temperature that is between about 50° C. and about 100° C., the inert polymeric composition 20 can be printed at an extrusion temperature of 140° C. to about 150° C. (e.g., about 150° C.). In other embodiments, the inert polymeric composition 20 can be printed at an extrusion temperature that is above the melting point of the polymer (no matter the $T_g$ of the polymer) such that the filament 32 melts and flows into the fabric 10 through the surface 12.

In certain embodiments, the fabric 10 is heated such that the inert polymeric composition 20 completely penetrates its thickness to form the inert polymeric coating 22. For example, the fabric 10 can be heated prior to printing, during printing, and/or after printing. In one embodiment, the fabric 10 is heated following printing with the inert polymeric composition 20 in an over at a temperature near the melting point of the polymer (e.g., within 15% of the melting point of the polymer) such that the polymer softens and flows through the thickness of the fabric 10.

Figure 2:
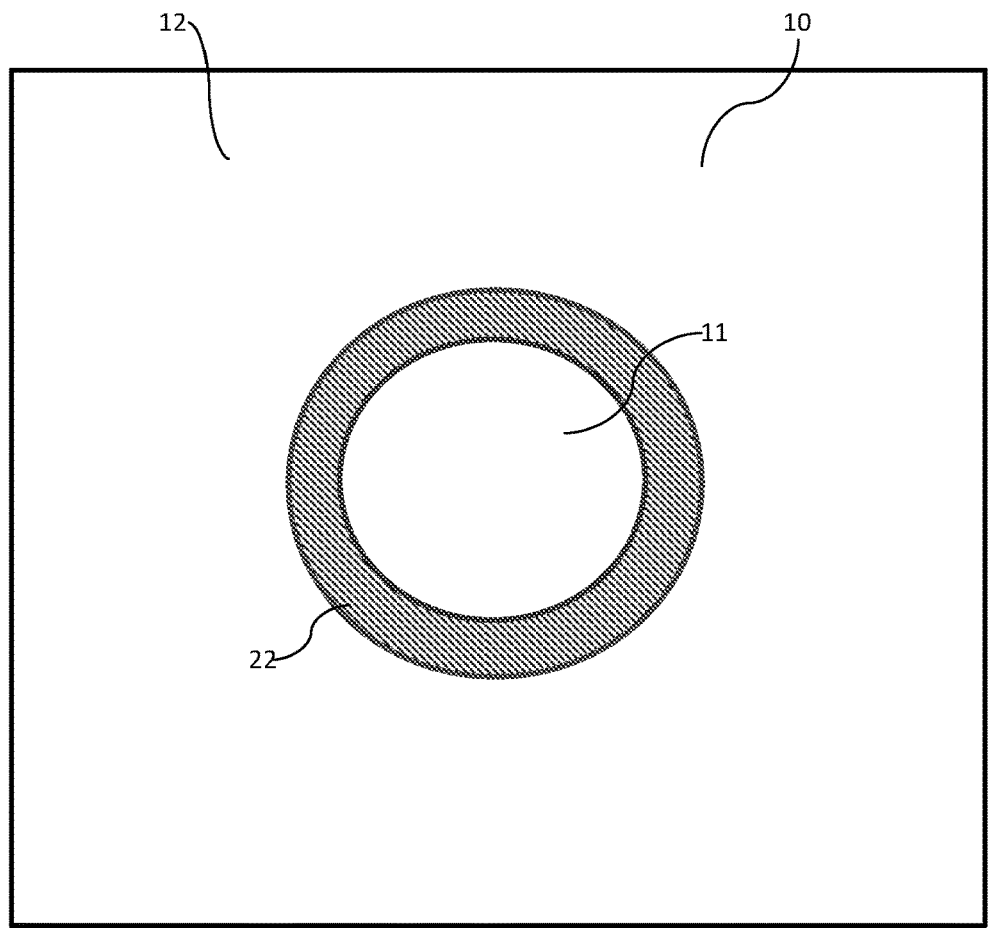
FIG. 2 is a top-down view of the exemplary fabric of FIG. 1.

The inert polymeric composition 20 in and on the fabric 10 is then cooled to form an inert polymeric coating 22 within and on the fabric 10, as shown in FIGS. 1 and 2. Cooling can be accomplished at room temperature (e.g., about 25° C.) up to the melting point of the polymer. In most embodiments, cooling can be achieved by heating the inert polymeric composition up to 100° C.

Generally, the polymer of the inert polymeric composition 20 can be composed of any polymer resin suitable for permeating the fabric 10 during printing while remaining inert to the analyte of the sample. In one embodiment, the polymer resin includes a polylactic acid (PLA) polymer (e.g., PLA having a Tg of about 60° C. to about 65° C. and a melting temperature of about 150° C. to about 180° C.). In one embodiment, a homopolymer of 2-oxepanone (i.e., a polycaprolactone) can be utilized. Polycaprolactone is a biodegradable polyester with a low melting point (e.g., around 60° C.) and a low glass transition temperature (e.g., around −60° C.). Such a polycaprolactone is available commercially under the name LEXIBLE from Perstorp Polyols, Inc., Toledo, Ohio.

The inert polymeric composition 20 can be applied to one or both of the surfaces 12, 14 of the fabric 10, depending on the several factors including but not limited to the thickness of the fabric, the viscosity of the inert polymeric composition, the composition of either or both the fabric and the inert polymeric composition, etc. In one particular embodiment, the inert polymeric composition 20 is printed onto both the first surface 12 and the second surface 14, as well as saturates the thickness of the fabric 10 from the first surface 12 to the second surface 14.

The inert barrier composition 20 can be applied to the fabric 10 at any amount sufficient to saturate the thickness of the fabric 10, and upon drying, prevent migration of a liquid sample applied out of the sample area. In particular embodiments, the inert polymeric composition 20 is applied at an add-on weight of about 1% to about 10%, such as about 1% to about 5%.

Once dried and solidified, the inert polymeric composition 20 completely surrounds the protected portion 11 throughout the thickness of the fabric 10 in order to inhibit any substantial flow of a sample through the inert polymeric composition 20 out of the sample area 30.

Although shown as forming a ring, the inert polymeric composition 20 can for any suitable shape with any suitable size in the fabric 10.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method of forming a sample area on a fabric, the method comprising:

printing a filament onto a first surface of the fabric to form the sample area, wherein the filament comprises an inert polymeric composition;

cooling the inert polymeric composition to form an inert polymeric coating in the fabric such that the sample area is completely surrounded by the inert polymeric coating.

2. The method of claim 1, wherein the filament is printed at an extrusion temperature, and wherein the inert polymeric coating comprises a polymer having a glass transition temperature that is less than the extrusion temperature.

3. The method of claim 2, wherein the extrusion temperature is about 100° C. to about 200° C.

4. The method of claim 2, wherein the extrusion temperature is about 125° C. to about 150° C.

5. The method of claim 2, wherein the glass transition temperature of the polymer is about 50° C. and about 100° C.

6. The method of claim 2, wherein the polymer has a melting temperature that is greater than the extrusion temperature.

7. The method of claim 1, wherein the polymer comprises a polylactic acid.

8. The method of claim 1, wherein the fabric defines a first surface and a second opposite surface, and wherein the filament is printed onto both the first surface and the second surface.

9. The method of claim 1, wherein the inert polymeric composition saturates the fabric around the sample area.

10. The method of claim 1, wherein the fabric comprises a woven fabric.

11. The method of claim 10, wherein the fabric comprises cotton fibers, nylon fibers, polyester fibers, silk fibers, or mixtures thereof.

12. The method of claim 1, wherein cooling the inert polymeric composition is achieved a cooling temperature that is less than about 100° C.

13. The method of claim 1, further comprising:
applying a blood sample to the sample area, wherein the blood sample saturates the fabric in the sample area but is prevented from migrating out of the sample area by the inert polymeric coating.

14. The method of claim 1, further comprising:
preheating the fabric to a temperature within 20% of the extrusion temperature.

15. The method of claim 1, further comprising:
heating the fabric during printing to a temperature within 20% of the extrusion temperature.

16. The method of claim 1, further comprising:
following printing, heating the fabric to a temperature sufficient to cause the polymer to soften and flow throughout the thickness of the fabric.

17. The method of claim 1, wherein the polymer has a melting temperature that is less than the extrusion temperature.

18. The method of claim 17, wherein the polymer comprises a homopolymer of 2-oxepanone.

* * * * *